(12) United States Patent
Wang et al.

(10) Patent No.: US 10,755,905 B2
(45) Date of Patent: Aug. 25, 2020

(54) QUALITATIVE AND QUANTITATIVE MASS SPECTRAL ANALYSIS

(75) Inventors: Yongdong Wang, Wilton, CT (US); Ming Gu, Yardley, PA (US)

(73) Assignee: CERNO BIOSCIENCE LLC, Las Vegas, NV (US)

(*) Notice: Subject to any disclaimer, the term of this patent is extended or adjusted under 35 U.S.C. 154(b) by 444 days.

(21) Appl. No.: 11/718,235

(22) PCT Filed: Oct. 28, 2005

(86) PCT No.: PCT/US2005/039186
§ 371 (c)(1),
(2), (4) Date: Apr. 28, 2007

(87) PCT Pub. No.: WO2006/050226
PCT Pub. Date: May 11, 2006

(65) Prior Publication Data
US 2009/0076737 A1 Mar. 19, 2009

Related U.S. Application Data

(60) Provisional application No. 60/623,114, filed on Oct. 28, 2004, provisional application No. 60/670,182, (Continued)

(51) Int. Cl.
*G01N 30/72* (2006.01)
*H01J 49/00* (2006.01)
(Continued)

(52) U.S. Cl.
CPC ...... *H01J 49/0009* (2013.01); *G01N 33/6848* (2013.01); *G06K 9/00543* (2013.01); *H01J 49/0036* (2013.01); *B01D 59/44* (2013.01)

(58) Field of Classification Search
CPC . G01N 33/6848; G01N 30/72; H01J 49/0036; H01J 49/0009; G06K 9/00543; B01D 59/44
(Continued)

(56) References Cited

U.S. PATENT DOCUMENTS 5,303,165 A 4/1994 Ganz et al.
6,138,082 A 10/2000 Wang et al.
(Continued)

OTHER PUBLICATIONS

Samuelsson, J et al., Modular, scriptable and automated analysis tools for high-throughput peptide mass fingerprinting, Bioinformatics, Aug. 2004, v.20,#18, p. 3628-35.
(Continued)

*Primary Examiner* — Mohamed Charioui

(57) ABSTRACT

A method for analyzing data from a mass spectrometer comprising acquiring raw profile mode data containing one or more ions and their isotopes in a mass spectral range; calculating theoretical isotope distributions for all ions of interest including native or labeled ions based on their molecular composition; convoluting the theoretical isotope distributions with target peak shape function specified during instrument calibration, actual peak shape functions, or approximated peak shape functions, to obtain theoretical isotope profiles for all ions; constructing a peak component matrix of relevant theoretical isotope profiles included as peak components; performing a weighted multiple linear regression between the profile mode data and the peak component matrix; and reporting regression coefficients as relative concentrations for each of the ions, or ranking these ions based on fitting statistics as search results. A mass spectrometer system (FIG. 1) operating in accordance with the method. Medium having computer code for operating the spectrometer.

48 Claims, 12 Drawing Sheets

Related U.S. Application Data filed on Apr. 11, 2005, provisional application No. 60/685,129, filed on May 29, 2005.

(51) Int. Cl.
*G06K 9/00* (2006.01)
*G01N 33/68* (2006.01)
*B01D 59/44* (2006.01)

(58) Field of Classification Search
USPC ......... 702/17, 23, 27, 30, 85, 179, 181–183; 250/281, 282, 286, 424
See application file for complete search history.

(56) References Cited

U.S. PATENT DOCUMENTS

| | | |
|---|---|---|
| 6,188,064 B1 | 2/2001 | Koester |
| 6,188,965 B1* | 2/2001 | Mayo et al. ................. 702/27 |
| 6,983,213 B2 | 1/2006 | Wang .............................. 702/85 |
| 2003/0109990 A1 | 6/2003 | Axelsson |
| 2004/0143402 A1* | 7/2004 | Colinge et al. ................. 702/19 |
| 2006/0136158 A1* | 6/2006 | Goldberg ............ H01J 49/0009 702/76 |
| 2006/0249668 A1* | 11/2006 | Goldberg et al. ............. 250/281 |
| 2010/0057372 A1* | 3/2010 | Fagerquist ......... G01N 33/6851 702/20 |

OTHER PUBLICATIONS

Berndt P, et al., Reliable automatic protein identification from matrix-assisted laser desorption/ionization mass spectrometric peptide fingerprints, Electrophoresis, Wiley Interscience, Dec. 1999, v.20, pp. 3521-26.

Stein S E, An Integrated Method for spectrum extraction and and compound identi-from gas chromatograhy/mass spectrometry data, J. Amer. Soc. M.S., v.10, pp. 770-81.

* cited by examiner

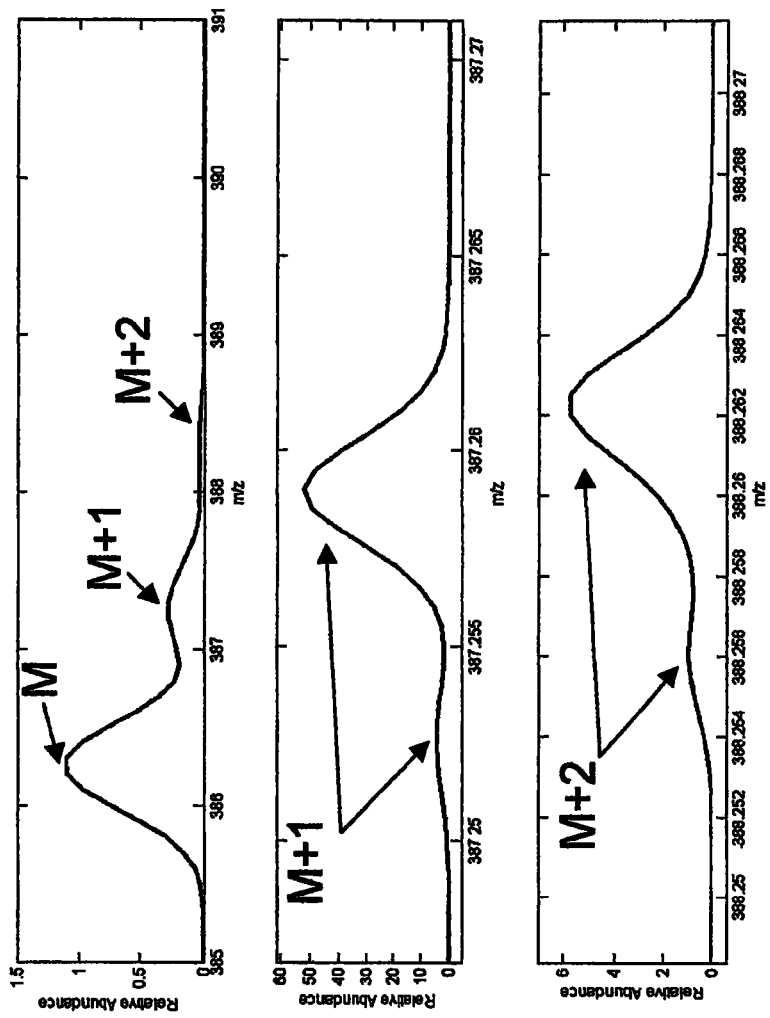

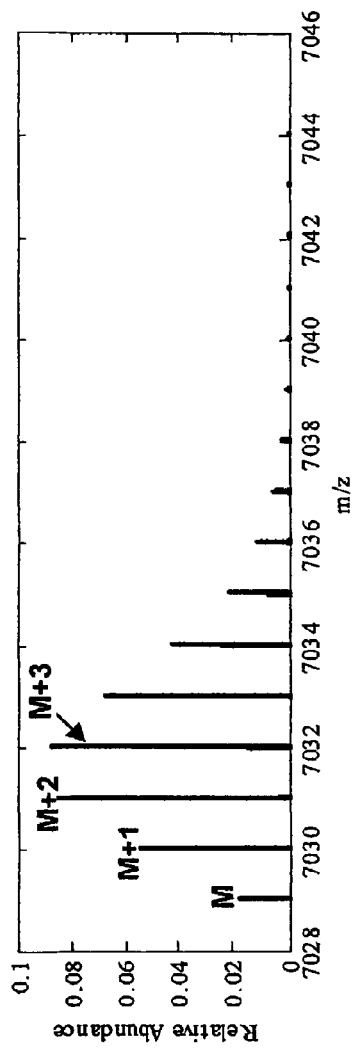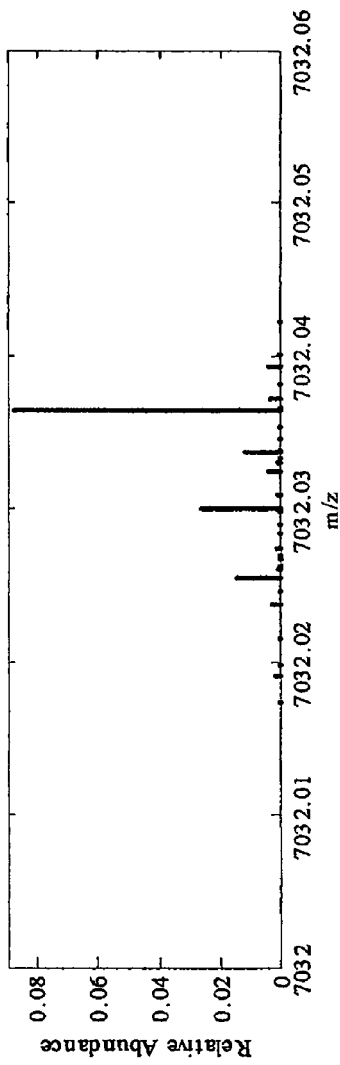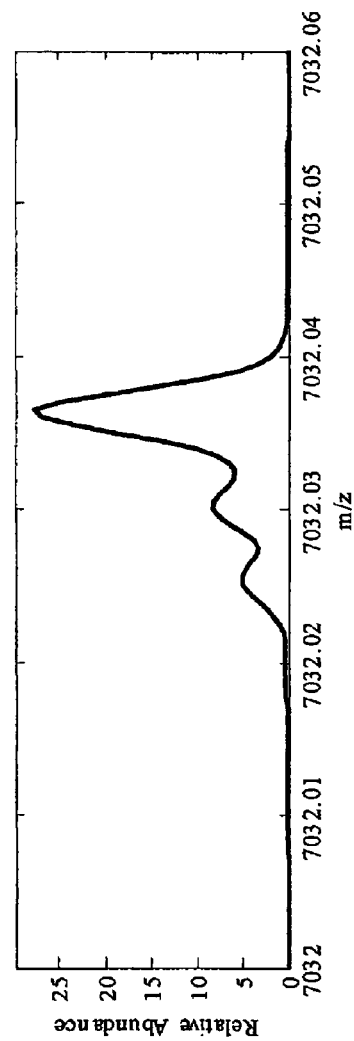
Fig. 3A
Fig. 3B
Fig. 3C

| Mono Mass | mDa | PPM | Formula | RMSE |
|---|---|---|---|---|
| 402.2508 | 0.1 | 0.2 | C20 H38 N3 F P S | 23997 |
| 402.2513 | -0.4 | -1.0 | C21 H42 N P2 S | 23132 |
| 402.2505 | 0.4 | 1.0 | C21 H32 N5 O3 | 15620 |
| 402.2514 | -0.5 | -1.2 | C16 H35 N5 O F3 S | 37679 |
| 402.2504 | 0.5 | 1.2 | C19 H40 N O F2 P Cl | 108065 |
| 402.2503 | 0.6 | 1.5 | C19 H34 N5 F2 S | 25033 |
| 402.2502 | 0.7 | 1.7 | C18 H40 N O2 F2 P2 | 33948 |
| 402.2517 | -0.8 | -2.0 | C18 H33 N5 O4 F | 26952 |
| 402.2499 | 1 | 2.5 | C18 H36 N3 O F3 Cl | 108546 |
| 402.2520 | -1.1 | -2.7 | C17 H39 N3 O F2 P S | 35951 |
| 402.2521 | -1.2 | -3.0 | C18 H39 N3 F2 S Cl | 121445 |
| 402.2497 | 1.2 | 3.0 | C17 H36 N3 O2 F3 P | 35924 |
| 402.2522 | -1.3 | -3.2 | C19 H37 N3 O4 P | 25219 |
| 402.2523 | -1.4 | -3.5 | C20 H37 N3 O3 Cl | 107704 |
| 402.2525 | -1.6 | -4.0 | C18 H43 N O F P2 S | 34285 |
| 402.2493 | 1.6 | 4.0 | C22 H39 N F P Cl | 105022 |
| 402.2526 | -1.7 | -4.2 | C19 H43 N F P S Cl | 121107 |
| 402.2492 | 1.7 | 4.2 | C16 H32 N5 O2 F4 | 37931 |
| 402.2491 | 1.8 | 4.5 | C21 H39 N O F P2 | 19622 |
| 402.2528 | -1.9 | -4.7 | C15 H34 N5 O5 F2 | 42629 |
| 402.2490 | 1.9 | 4.7 | C18 H38 N O4 F2 S | 35279 |
| 402.2488 | 2.1 | 5.2 | C21 H35 N3 F2 Cl | 105124 |
| 402.2486 | 2.3 | 5.7 | C20 H35 N3 O F2 P | 21148 |
| 402.2486 | 2.3 | 5.7 | C16 H44 N3 P4 | 41375 |
| 402.2484 | 2.5 | 6.2 | C20 H41 N3 Br | 320799 |
| 402.2483 | 2.6 | 6.5 | C15 H37 N5 O5 Cl | 114970 |

Fig. 7

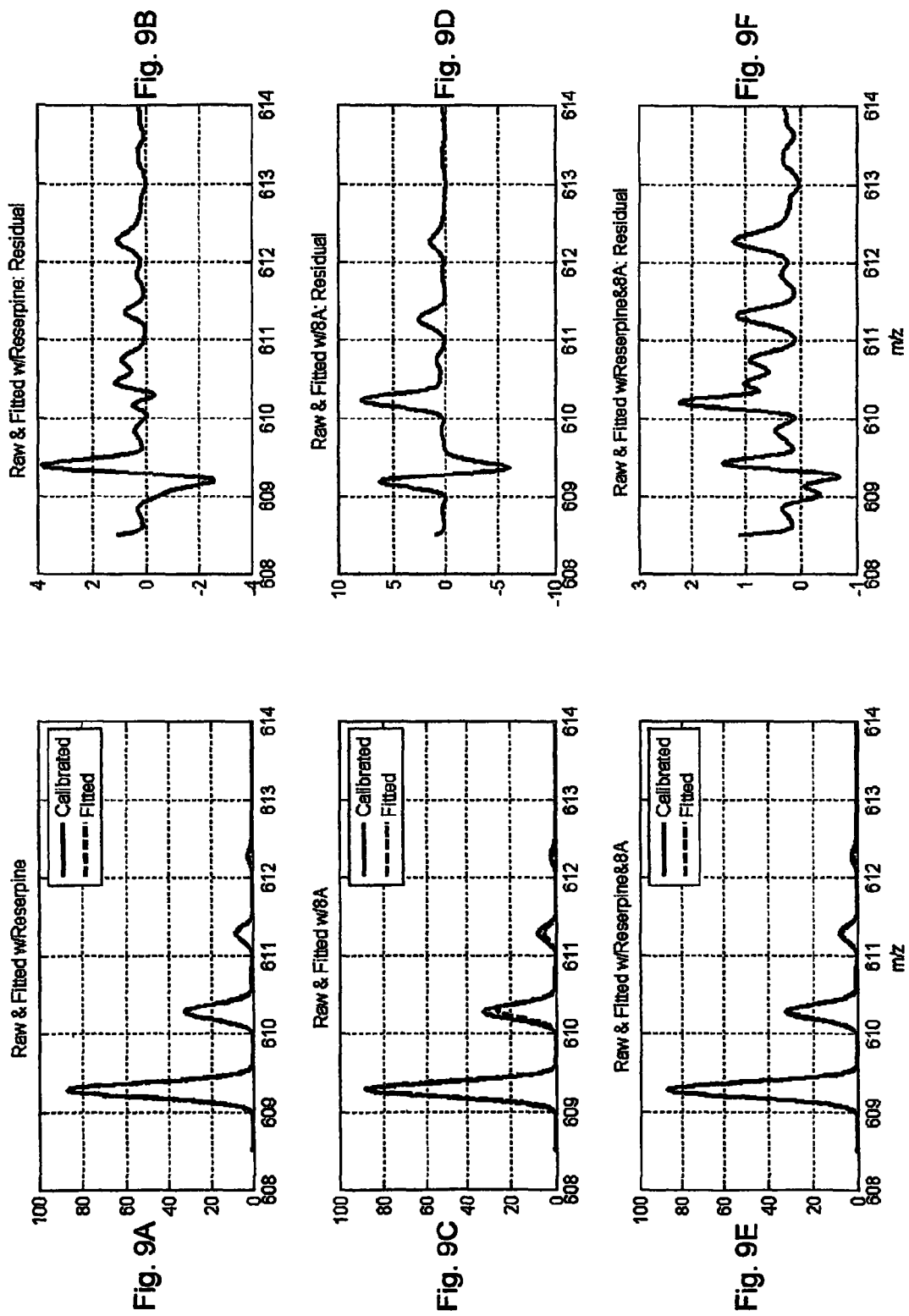

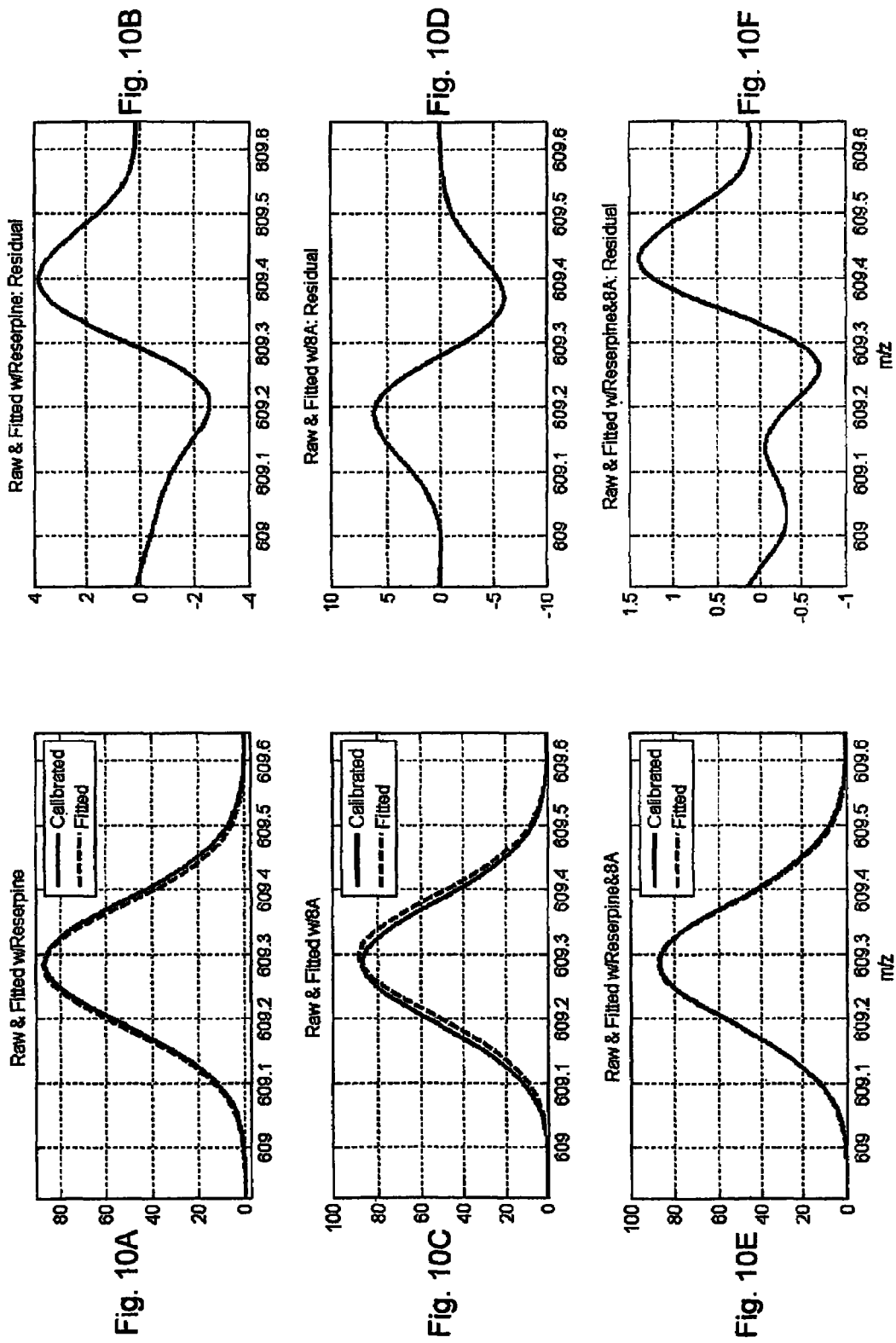

QUALITATIVE AND QUANTITATIVE MASS SPECTRAL ANALYSIS

This application is a United States national stage application, filed under 35 U.S.C. §371, of International Patent Application PCT/US2005/039186.

This application claims priority from U.S. provisional application Ser. Nos. 60/623,114 filed on 28 Oct. 2004; 60/670,182 filed on 11 Apr., 2005, and 60/685,129 filed on 29 May, 2005. The entire teachings of these applications are hereby incorporated by reference, in their entireties.

CROSS-REFERENCE TO RELATED APPLICATIONS

This application is related to the following patent applications:

U.S. Ser. No. 10/689,313 filed on 20 Oct. 2003 and International Patent PCT/US2004/034618 filed on 20 Oct. 2004 which claims priority therefrom and designates the United States of America as an elected state.

U.S. Provisional patent applications 60/466,010; 60/466,011 and 60/466,012 all filed on 28 Apr., 2003, and International Patent Applications PCT/US2004/013096 and PCT/US2004/013097 both filed on 28 Apr., 2004 and designating the United States of America as an elected state.

The entire teachings of these patent applications are hereby incorporated herein by reference, in their entireties.

BACKGROUND OF THE INVENTION

Field of the Invention

The present invention relates to improvements and applications with respect to the teachings of the above referenced patent applications in the field of general mass spectrometry including ion mobility spectrometry (IMS).

Background Art

The background art has been described in the above referenced patent applications dealing with mass spectrometry in general including ion mobility spectrometry (IMS) where the vacuum is absent from the general purpose system illustrated in FIG. 1.

SUMMARY OF THE INVENTION

The present application is directed to the following improvements:
1. A new search algorithm for molecular formula determination with applications from metabolite identification to peptide or protein identification by taking advantage of multiple observable isotopes and the profile mode mass spectral data available.
2. The use of this search algorithm in the deconvolution of overlapped isotopes or clusters for the purpose of identifying and quantifying the ions involved.
3. A novel algorithm for unbiased and accurate quantitation of all relevant components in isotope labeling experiment through the use of a mass spectrometer by incorporating the knowledge of the naturally occurring and labeled isotopes and the profile mode mass spectral data available.

Each of these aspects will be described below along with preliminary results to demonstrate their utilities. For the purpose of easily describing the inventions made, no distinction will be made between the neutral and the ion form of a molecule or its fragments with the understanding that, for example, it typically requires an added proton to convert a neutral into the corresponding positive ion in order to measure it in a mass spectrometer.

Contrary to conventional wisdom, when proper calibration of a profile mode spectrum (not a centroiding or stick spectrum), as described herein, is used, the method in accordance with the invention allows for the highly selective identification of an unknown ion and its elemental composition with a conventional mass spectrometer of approximately unit mass resolution. This is especially useful in identifying drugs, their metabolites, degradation products, impurities, peptides, proteins, and other molecules.

In accordance with the invention, it is also possible to quantitatively analyze a mixture of ions where their monoisotopic masses differ by as little as a small fraction of 1 Da on a unit mass resolution instrument. This is especially useful in the quantitative analysis of drugs, their metabolites, peptides, proteins and other molecules through either isotope labels or other mass tags or derivatizations.

BRIEF DESCRIPTION OF THE DRAWINGS

The foregoing aspects and other features of the present invention are explained in the following description, taken in connection with the accompanying drawings, wherein like numerals indicate like components, and wherein:

FIG. 2A is a table of exact isotope distribution for a small molecule drug Buspirone;

FIG. 2B is the simulated mass spectral profile mode data for Buspirone on a unit mass resolution system;

FIG. 2C is the simulated mass spectral profile mode data for Buspirone M+1 isotope cluster on a very high resolution system;

FIG. 2D is the simulated mass spectral profile mode data for Buspirone M+2 isotope cluster on the same high resolution system.

FIG. 3A is the theoretically calculated isotope distribution for a larger Hirudin ion;

FIG. 3B is a zoomed-in region of the M+3 isotope cluster;

FIG. 3C is the simulated mass spectral profile mode data for the M+3 isotope cluster on a very high resolution system.

FIG. 7 is the hit list from a conventional elemental search based on accurate monoisotopic mass of Buspirone hydroxygenated metabolite.

FIGS. 9A, 9C, and 9E are calibrated data measured on a higher resolution qTOF system and the fitted version with Reserpine, 8-alanine, and both, respectively.

FIGS. 9B, 9D, and 9F are the corresponding fitting residuals of FIGS. 9A, 9C, and 9E, respectively.

FIG. 10A to 10F are the zoomed in versions of FIG. 9A to 9F.

DETAILED DESCRIPTION OF THE PREFERRED EMBODIMENTS

Figure 1:
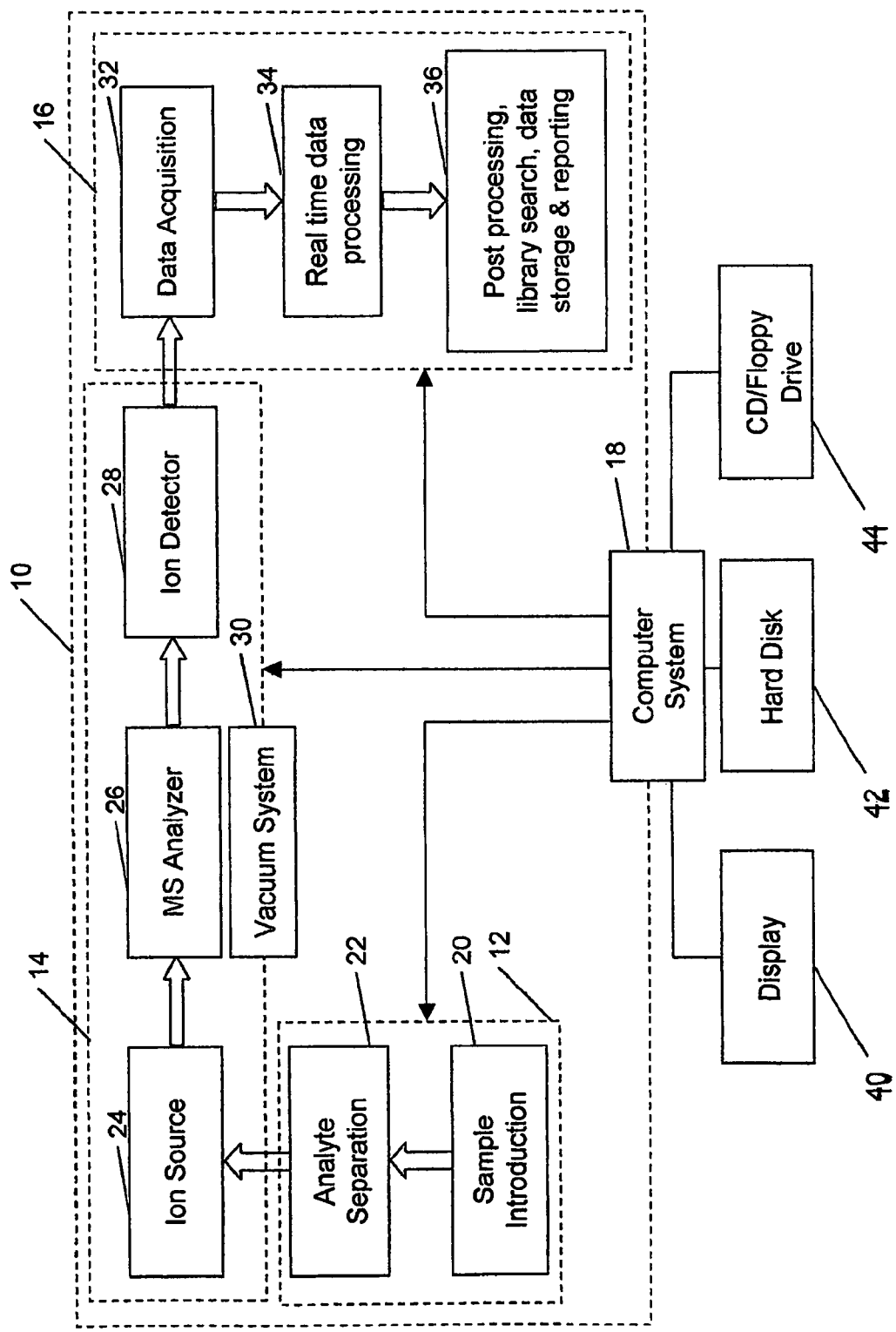
FIG. 1 is a block diagram of an analysis system in accordance with the invention, including a mass spectrometer.

Referring to FIG. 1, there is shown a block diagram of an analysis system 10, that may be used to analyze proteins or other molecules, as noted above, incorporating features of the present invention. Although the present invention will be described with reference to the embodiments shown in the drawings, it should be understood that the present invention can be embodied in many alternate forms of embodiments. In addition, any suitable types of components could be used.

Analysis system 10 has a sample preparation portion 12, a mass spectrometer portion 14, a data analysis system 16, and a computer system 18. The sample preparation portion 12 may include a sample introduction unit 20, of the type that introduces a sample containing proteins or peptides of interest to system 10, such as Finnigan LCQ Deca XP Max, manufactured by Thermo Electron Corporation of Waltham, Mass., USA. The sample preparation portion 12 may also include an analyte separation unit 22, which is used to perform a preliminary separation of analytes, such as the proteins to be analyzed by system 10. Analyte separation unit 22 may be any one of a chromatography column, an electrophoresis separation unit, such as a gel-based separation unit manufactured by Bio-Rad Laboratories, Inc. of Hercules, Calif., and is well known in the art. In general, a voltage is applied to the unit to cause the proteins to be separated as a function of one or more variables, such as migration speed through a capillary tube, isoelectric focusing point (Hannesh, S. M., *Electrophoresis* 21, 1202-1209 (2000), or by mass (one dimensional separation)) or by more than one of these variables such as by isoelectric focusing and by mass (two dimensional separation). An example of the latter is known as SDS-PAGE.

The mass spectrometer portion 14 may be a conventional mass spectrometer and may be any one available, but is preferably one of MALDI-TOF, quadrupole MS, ion trap MS, qTOF, TOF/TOF, or FTICR-MS. If it has a MALDI or electrospray ionization ion source, such ion source may also provide for sample input to the mass spectrometer portion 14. In general, mass spectrometer portion 14 may include an ion source 24, a mass analyzer 26 for separating ions generated by ion source 24 by mass to charge ratio, an ion detector portion 28 for detecting the ions from mass analyzer 26, and a vacuum system 30 for maintaining a sufficient vacuum for mass spectrometer portion 14 to operate efficiently. If mass spectrometer portion 14 is an ion mobility spectrometer, generally no vacuum system is needed.

The data analysis system 16 includes a data acquisition portion 32, which may include one or a series of analog to digital converters (not shown) for converting signals from ion detector portion 28 into digital data. This digital data is provided to a real time data processing portion 34, which process the digital data through operations such as summing and/or averaging. A post processing portion 36 may be used to do additional processing of the data from real time data processing portion 34, including library searches, data storage and data reporting.

Computer system 18 provides control of sample preparation portion 12, mass spectrometer portion 14, and data analysis system 16, in the manner described below. Computer system 18 may have a conventional computer monitor 40 to allow for the entry of data on appropriate screen displays, and for the display of the results of the analyses performed. Computer system 18 may be based on any appropriate personal computer, operating for example with a Windows® or UNIX® operating system, or any other appropriate operating system. Computer system 18 will typically have a hard drive 42, on which the operating system and the program for performing the data analysis described below is stored. A drive 44 for accepting a CD or floppy disk is used to load the program in accordance with the invention on to computer system 18. The program for controlling sample preparation portion 12 and mass spectrometer portion 14 will typically be downloaded as firmware for these portions of system 10. Data analysis system 16 may be a program written to implement the processing steps discussed below, in any of several programming languages such as C++, JAVA or Visual Basic.

Mass Spectral Fitting for Molecular Search

Mass spectrometry with highly accurate ion mass measurement offers a quick and unique way for the determination of elemental compositions or molecular formulas, which can offer great insights for the ions under the measurement, ranging from unknown metabolite identification to DNA or protein identification or sequencing to degradation product or impurity identification.

The conventional approach for molecular formula determination starts with high mass accuracy determination of a mass spectral peak of interest and searches for all possible formulas within a given mass error window (typically measured as parts per million or ppm), for example, +/−5 ppm from the determined mass. Since all elements in the periodic table have their exact masses carefully measured for the lowest isotope, the elemental composition or molecular search algorithm amounts to the following optimization $$\min_{p_i, n_i} \left| m - \sum_{i=1}^{p} n_i m_i \right| \qquad \text{Equation 1}$$

where m is the measured accurate monoisotopic mass for the ion of interest, $n_i$ is the number of elements for the i-th element, and $m_i$ is the lowest exact mass among all isotopes of this i-th element This optimization problem can typically be solved through integer programming, which can be drastically sped-up through the introduction of such constraints as the lowest possible and the highest possible number of each element n and the maximal number of elements p. Other constraints may include the existence of rings, double bonds, or a limited selection of possible elements (for example, a typical small molecule drug may contain only C, H, N, O, S, P, Cl etc.). For larger molecules such as proteins or peptides, typically the search of the form given in Equation 1 is performed for a given protein or peptide library, which automatically constrains the search to a set of known proteins or peptides previously identified or hypothesized.

This approach works well under the following conditions:
1. The mass spectrometer is of high resolution, typically a quadruple time-of-flight (qTOF) system or FTMS, allowing for the monoisotopic peak of an ion to be baseline-resolved from its other isotopes in order to achieve high mass accuracy and facilitate the compound identification.
2. High signal to noise in the measurement of the monoisotopic peak without saturation or nonlinearity.
3. The monoisotopic peak is pure and free from any interfering ions or isobaric interferences.
4. The molecule being searched is generally a small molecule with molecular weight less than 1000 Da where the only pure isotope peak is the monoisotopic peak which is typically the most abundant peak.
5. A sufficiently symmetrical peak shape, available after extensive tuning of the instrument involving even hand-tuning of specific voltages for reliable mass determination.
6. A reliable and unbiased algorithm for mass determination.

It has been pointed out in the patent applications referenced above that high mass accuracy is available on even unit mass resolution systems where the monoisotopic peak is not baseline-resolved from other isotope peaks and it is possible to determine the accurate mass of the monoisotopic peak in the presence of interfering isotope peaks. In spite of all the benefits of the mass spectral instrument calibration and peak analysis disclosed in the applications referenced above, it should be noted that the process of mass (and area) determination from a continuum mass spectral response is one of deconvolution that is prone to error propagation and noise amplification. This becomes particularly problematic for M+1 or M+2 isotope peaks where there are many individual isotopes located very close in masses to each other.

FIG. 2A shows the theoretical isotope distribution for a small molecule drug Buspirone with molecular ion formula $C_{21}H_{32}N_5O_2^+$, where the monoisotope (386.2556 Da, before adjusting the mass of a lost electron, 0.0005486 Da) is the most abundant and composed of a single isotope. All other isotope peaks are weaker and composed of multiple individual isotopes that are at least about 1 Da from the monoisotope and easily separated from the monoisotope on a unit mass resolution system as shown in FIG. 2B. The separation of the 2 most abundant isotopes under the M+1 peak, however, would have required a resolving power of at least $387.25/(0.0064/2)=121,016$, a feature only available on the highest resolution FTMS systems where some sensitivity may have to be compromised.

FIG. 2C shows the simulated mass spectrum for the M+1 isotopes at such high resolving power that the two most abundant isotopes within the cluster can be visually observed For the M+2 peak cluster as shown in FIG. 2D, however, the two isotopes at 388.2560 and 388.2597 Da are no longer separated even at such high resolution, resulting in some ambiguity in peak picking or centroiding which can adversely impact molecular formula searches based on peak picking results alone. The profile data in FIG. 2D, on the other hand, contains all relevant information about the M+2 isotope cluster of this molecule and provides a unique signature on which a search for this molecule may be based.

For a larger molecule like Hirudin, its molecular ion $C_{289}H_{446}N_{84}O_{109}S_6^+$ with monoisotopic mass of 7029.02630 Da is large enough that the monoisotopic peak is no longer the most abundant, while its other isotope peaks become increasingly complex with contributions from many other isotopes. FIG. 3A shows the 1,000 most abundant isotopes as stick spectrum and FIG. 3B shows a zoomed in version of the most abundant M+3 cluster. Even at the high resolving power of 121,016, the simulated spectrum for the M+3 cluster shown in FIG. 3C reveals just a few of the many isotopes contributing to this cluster, resulting in ambiguity in peak picking or centroiding which may adversely impact a conventional molecular formula search. Again, the profile data in FIG. 3C, though not fully resolved, contains all relevant information about the M+3 cluster of this molecule and provides a unique signature on which a search for this molecule may be based.

For even larger molecules such as intact proteins analyzed in "top-down" proteomics, the monoisotope peak will become so small compared to other more abundant isotope clusters that it may not even be observable anymore given the instrument resolving power, the sensitivity, and the linear dynamic range. While one can still manage to get some form of overall mass measurement from the more abundant isotope clusters, this measurement no longer provides a unique accurate mass that one could depend on for reliable molecular formula search, due to the many 2Q unresolved isobaric interferences and the contribution of mass spectrometer peak shape functions to the observed mass spectral data.

Based on the comprehensive mass spectral calibration disclosed in U.S. Ser. No. 10/689,313 filed on 20 Oct. 2003 and International Patent PCT/US04/034618 filed on 20 Oct. 2004 which claims priority therefrom and designates the United States of America as an elected state, the peak analysis can still be performed on peaks with unresolved isobaric interferences to arrive at a unique accurate mass for the isotope clusters. Since the peak shape function has been converted into a symmetrical function after the calibration transformation, this unique accurate mass is in fact a weighted average of all the isotopes included in the cluster with their relative abundances as weights, i.e., a mathematically defined centroid. With the centroids for all isotope clusters clearly defined and calculated, one can in theory perform a molecular formula search based on the actual observed centroids and the theoretical centroids calculated from the corresponding isotope distributions given the elemental compositions. One may even incorporate the apparent peak areas for the identified peaks as weights into the subsequent searches and scoring based on centroid masses to reflect the relative abundances of these isotope clusters.

The match between observed centroid and theoretical centroid masses can be performed through a weighted least squares regression which will automatically provide some measurement for the goodness-of-fit or probability for the molecular formula assignment or library hit. The statistics and assignment of probabilities, however, become less rigorous or elegant or diagnostic due to the loss in information content during the peak analysis process where all unresolved isotopes are effectively binned together.

The details of a more preferred embodiment will now be presented that utilizes the full mass spectral information available for molecular formula or library search, search diagnostics, quantitative mixture analysis, and statistical measures, all without the peak centroding step.

Figure 4:
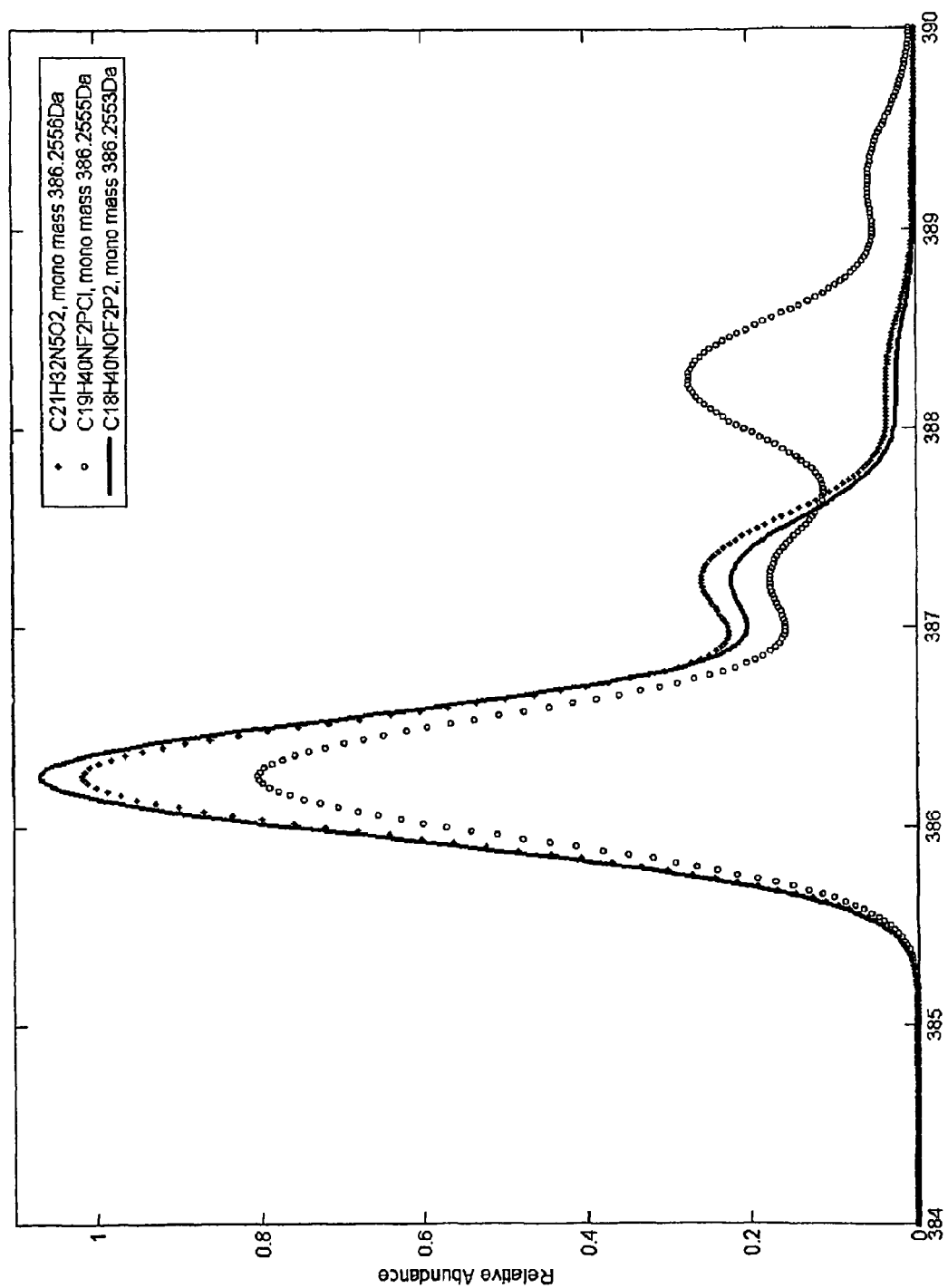
FIG. 4 is the theoretical isotope profile mode data at unit mass resolution for three candidate matches of Buspirone with all their monoisotopic masses within 1 ppm of each other.

While accurate mass of the monoisotopic peak is a very important piece of information for an ion, its other isotopes and the pattern in which they overlap provide crucial additional information about a particular ion, which when properly utilized, can further enhance the discrimination between this and other candidate molecules of even very similar monoisotopic masses. FIG. 4 shows the mass spectra of two ions with their monoisotopic masses within 1 ppm of that of the ion of interest (Buspirone in this example), but with very dissimilar spectral patterns due to the differences in their elemental compositions.

This invention described herein:
1. Takes advantage of the isotope patterns available for each molecule as additional information to discriminate among the many candidate molecules of very similar monoisotopic masses.
2. Avoids using peak picking and centroiding as the only means of molecular formula search and thus avoids an extra step of data processing where errors may occur and random noises may be amplified.
3. Makes possible the molecular formula or library search through continuum profile data by the use of comprehensive and total mass spectral calibration disclosed in U.S. Ser. No. 10/689,313 filed on 20 Oct. 2003 and International Patent PCT/US2004/034618 filed on 20 Oct. 2004 which claims priority therefrom and designates the United States of America as an elected state. The comprehensive mass spectral calibration allows for a highly accurate match of the mass as well as the peak shape functions.
4. This comprehensive mass spectral calibration enables molecular formula or library search on even unit mass resolution mass spectrometers, a unique feature generally thought of as being reserved for higher resolution systems.
5. On high resolution systems, molecular formula or library search can now be performed without identifying the monoisotope peak, which may be quite weak or even un-observable for large molecules such as peptides or proteins. Furthermore, molecular formula or library search can also be performed using any section of the isotope clusters that may contain many individual isotopes without physically separating them. It may even be possible to use a single isotope cluster, for example, the M+3 cluster from FIG. 3C, for a molecular formula or library search, especially when other clusters have poor signal to noise, nonlinearity, or significant overlaps from interferences.

Figure 5:
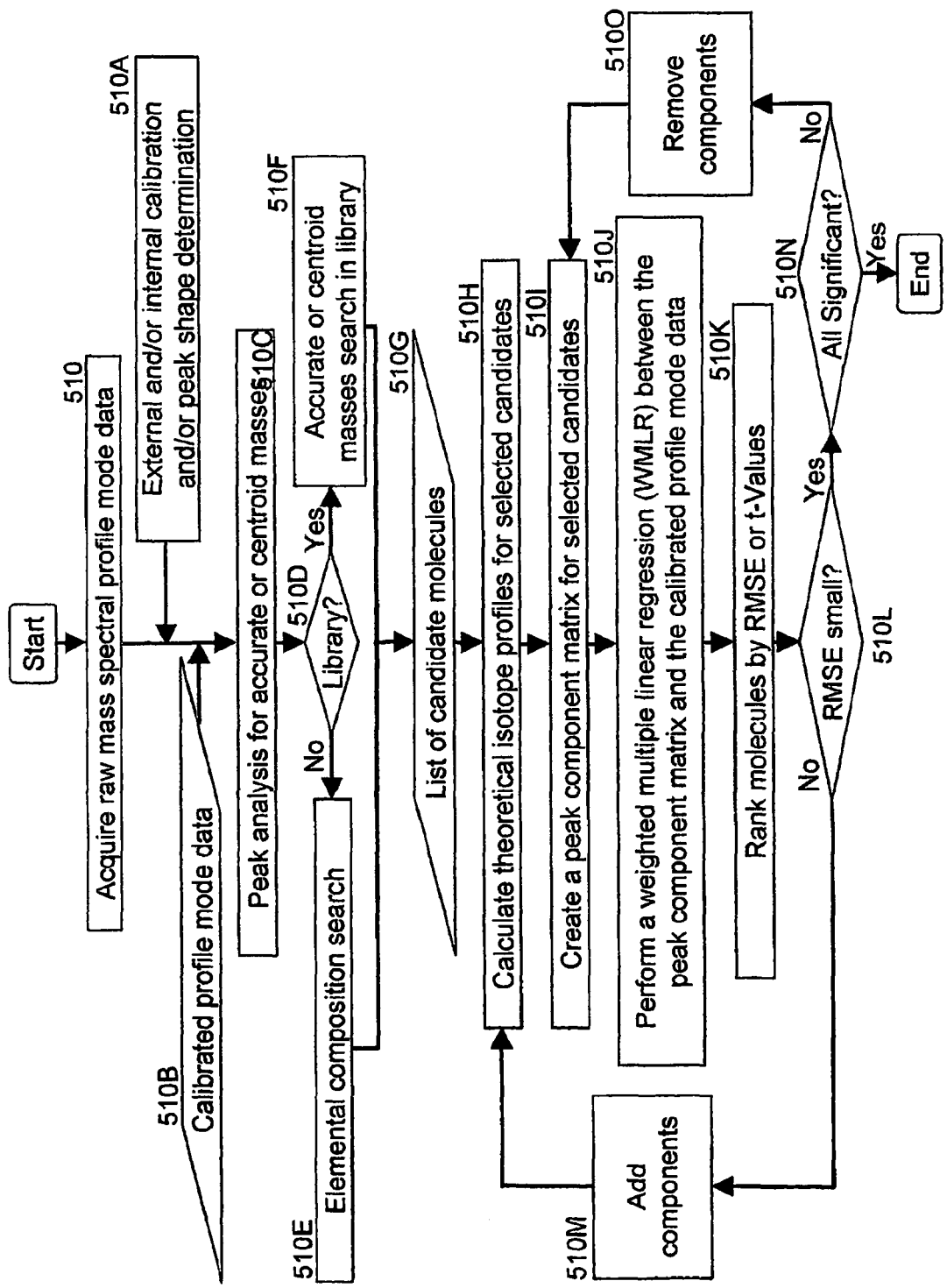
FIG. 5 is a flow chart for the highly selective compound identification process of this invention.
Figure 6A:
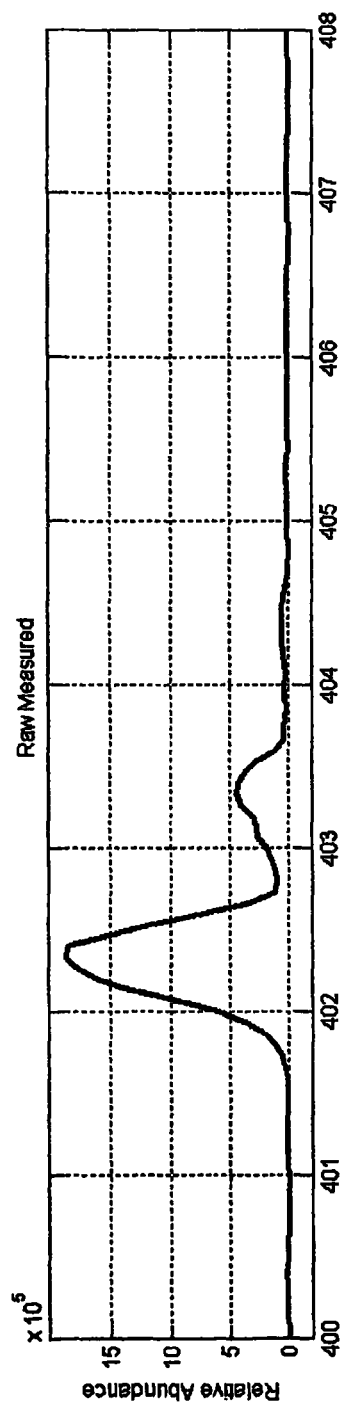
FIG. 6A is an acquired raw mass spectral profile mode data for the hydroxygenated metabolite of Buspirone.
Figure 6B:
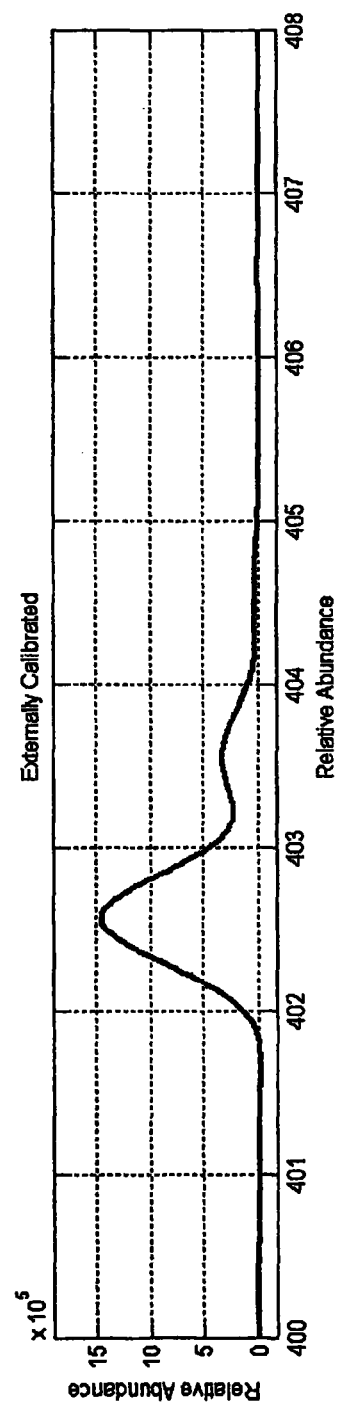
FIG. 6B is the externally calibrated version of the data of FIG. 6A.
Figure 6C:
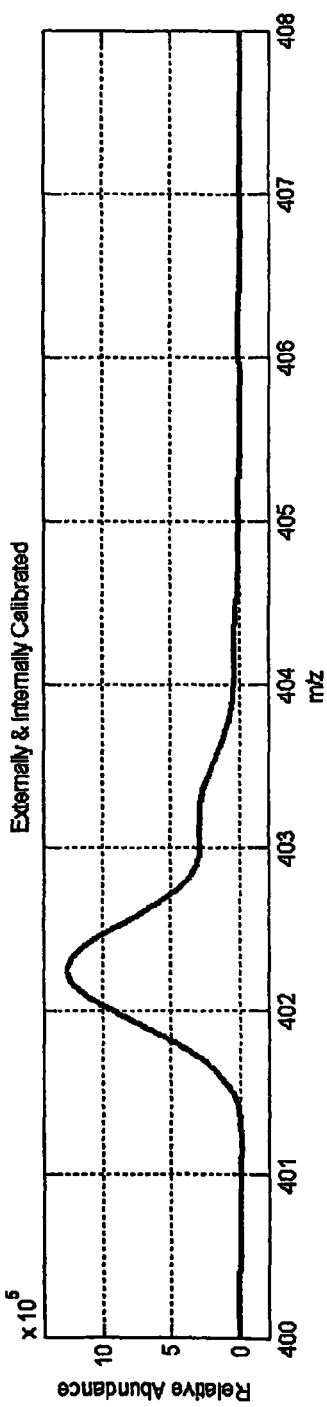
FIG. 6C is the internally and externally calibration version of the data of FIG. 6A.
Figure 8:
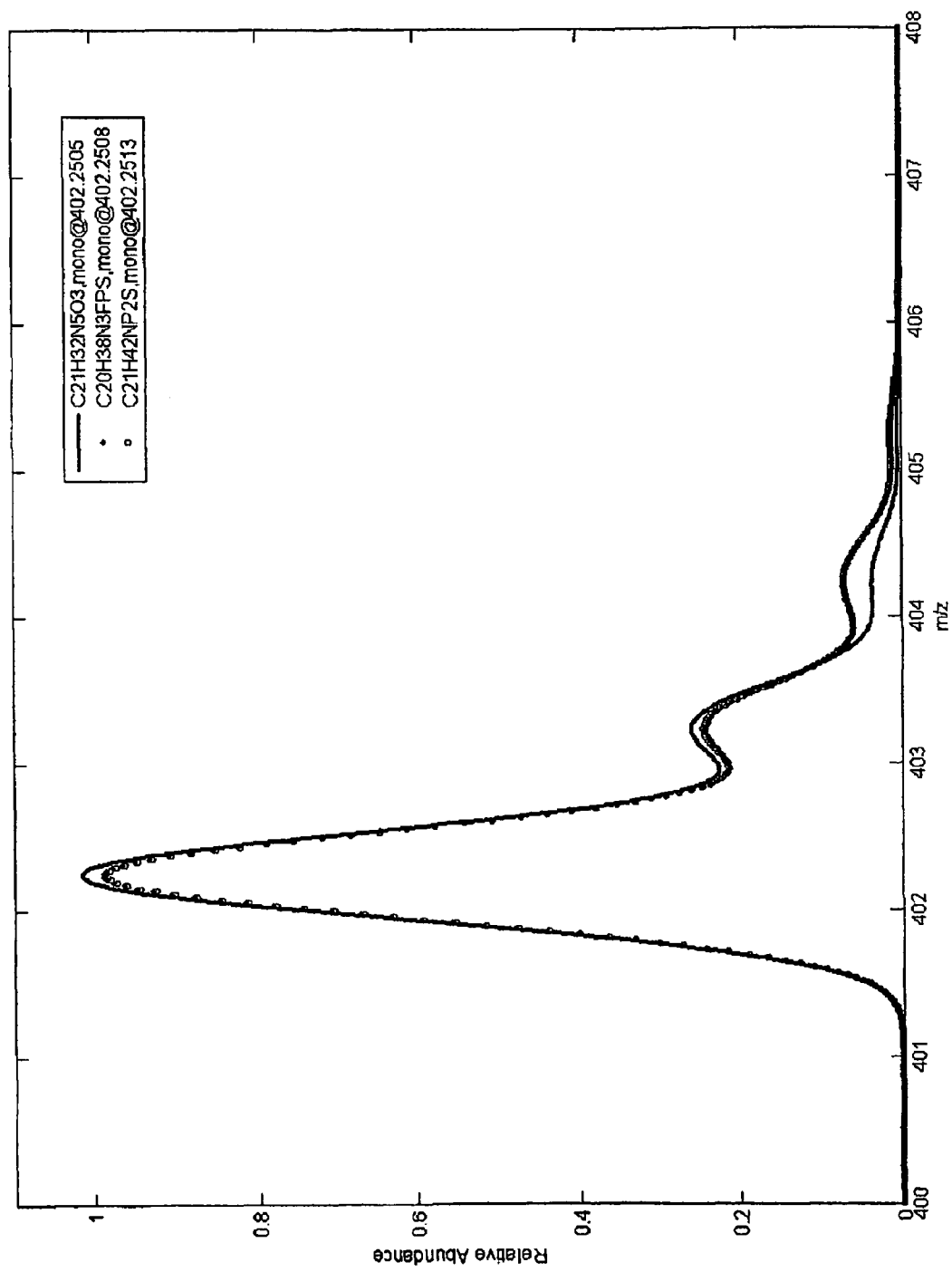
FIG. 8 is the theoretical isotope profile mode data at unit mass resolution for three candidate matches of the Buspirone hydroxygenated metabolite with their monoisotopic masses within 1 ppm of each other.

The specific steps are similar to what was disclosed in the PCT/US2004/013096 filed on 28 Apr., 2004 entitled "COMPUTATIONAL METHOD AND SYSTEM FOR MASS SPECTRAL ANALYSIS" and are described along with an example below:
1. Acquire raw mass spectral data in the profile mode with many points across a mass spectral peak. This raw mass spectral data may or may not have internal standard or standards included. FIG. 6A shows a section of such a raw mass spectral data corresponding to a metabolite of the drug Buspirone. This step is shown as 510 in the flowchart of FIG. 5.
2. Apply a total calibration filtering matrix developed earlier as part of an external or instrument calibration to the raw mass spectral data collected to correct for any mass axis error and transform the mass spectral peak shape function into a known peak shape function, preferably a mathematically definable symmetrical function. FIG. 6B shows the same section in FIG. 6A after external calibration. This step is shown as 510B in the flowchart of FIG. 5 where the calibration from 510A of FIG. 5 is applied.
3. If at least one internal standard is available, perform a new calibration using the at least one standard as the standard in a separate new instrument calibration (internal calibration). Apply this newly determined internal calibration to the externally calibrated data to obtain externally and internally calibration data. FIG. 6C shows the section in FIG. 6B after this additional internal calibration. This step is also shown as 510B in the flowchart of FIG. 5. If only the actual peak shape functions are determined without the comprehensive calibration either separately or while acquiring the raw profile mode mass spectral data (510A in FIG. 5), both step 2 and this step can be optionally by-passed with all subsequent data processing applied to raw profile mode data instead of calibrated profile mode data.
4. In searching for possible molecular formula or compound corresponding to the fully calibrated mass spectral data shown in FIG. 6C, one typically goes through a peak picking process, preferably one disclosed in the section starting from line 8 on page 32 of U.S. patent application Ser. No. 10/689,313 or PCT/US2004/034618 filed on 20 Oct. 2004 (section starting from line 14 of page 34), to generate a peak list containing peak mass locations as well as integrated peak areas. Either target peak shape functions or actual peak shape functions may be used for peak analysis, depending on whether the calibration data (510B in FIG. 5) are available. The monoisotopic peak mass thus calculated from the data trace in FIG. 6C is 402.2509 Da. A compositional search with elements C, H, N, O, S, P, Cl, and Br within a 5 ppm monoisotopic mass error window yields a list of 26 candidate molecules with $C_{20}H_{38}N_3FPS$ (monoisotopic mass 402.2508 Da, the wrong molecule) as the top hit, as shown in FIG. 7. These steps are shown as 510C-510D-510E-510G in the flowchart of FIG. 5. For larger molecules such as peptides or proteins, a search in a given library is more typically performed to generate a list of candidates following the steps outlined in 510C-510D-510F-510G of FIG. 5.
5. Instead of relying on monoisotopic mass for molecular formula determination, this aspect of the invention calculates the theoretical mass spectral isotope profile for each of the candidate molecules identified and compare this theoretical mass spectral profile with that of the actual isotope profile as acquired or after the calibration (external and/or internal calibration, step 510A and data 510B in FIG. 5). This calculation involves calculating the theoretical isotope distribution followed by convolution with either the target peak shape functions or actual peak shape functions, all defined in the comprehensive calibration process disclosed in the U.S. patent application Ser. No. 10/689,313 or PCT/US2004/034618 filed on 20 Oct. 2004. The actual mass spectral peak shape after calibration where applicable will be transformed to the target peak shape function. FIG. 8 shows the theoretical isotope profiles for the top three hits listed in FIG. 7, based on a calculating step 510H in FIG. 5.
6. Form a different peak component matrix P (page 32 of U.S. patent application Ser. No. 10/689,313 and page 34 in PCT/US2004/034618 filed on 20 Oct. 2004) for each of the candidate molecules listed in FIG. 7 by including any linear or nonlinear functions as possible baseline components and the corresponding theoretical isotope profile as the sole peak component. If a subset of the molecules are known, the theoretical isotope profiles of these known molecules can be calculated directly without elemental composition or library search and included in the peak component matrix to be treated just like baseline components. If there is evidence that the mass spectrum may have shifted after the most recent calibration (either external or internal), one may add one more component, the $1^{st}$ derivative of the actually measured or calibrated isotope profile, into the matrix P to account for any additional mass axis shift. This step is illustrated as 510I in FIG. 5.

7. A Weighted Multiple Linear Regression (WMLR, equation 6 on page 34 of U.S. patent application Ser. No. 10/689,313 and equation 6 on page 35 of /US2004/ 034618 filed on 20 Oct. 2004) is mow performed between the acquired raw or calibrated isotope profile (for example, FIG. 6C) and each peak component matrix using the inverse of the peak intensity variance w (page 34 of U.S. patent application Ser. No. 10/689, 313 and page 35 in PCT/US2004/034618 filed on 20 Oct. 2004) as weights. A fitting error (Root-Mean Squared Error or RMSE), t-value, correlation coefficient, or other statistic such as F-statistic is calculated from each regression (pages 35 and 39 of U.S. patent application Ser. No. 10/689,313 and on pages 36 and 39 in PCT/US2004/034618 filed on 20 Oct. 2004). This step is illustrated as 510J in FIG. 5.

8. The higher the t-value or the smaller the RMSE, the higher the chance for the molecule to be the correct one. FIG. 7 and FIG. 8 show that the correct formula $C_{21}H_{32}N_5O_3$ (monoisotopic mass 402.2505 Da) indeed provides the smallest fitting error among all 26 candidate molecules, even though the calculated monoisotopic mass 402.2509 Da is not the closest match to its exact mass of 402.2505 Da. This step is illustrated as 510K in FIG. 5.

This aspect of the invention eliminates intermediate and error-prone steps for molecular search, yielding more reliable results by taking into consideration of all the isotopes available, their relative abundances, and their differing masses. For smaller molecules such as drugs or their metabolites in the range of 200-600 mass range, this profile-based search offers significant advantages even though the monoisotopic peak is likely to be the most abundant for these molecules. For larger molecules such as proteins or peptides, the monoisotopic peak is typically not the most abundant if observable at all and the instrument resolution width (FWHM) typically increases on mass spectrometers such as TOF or FTMS while the isotope distribution becomes more complex, making peak analysis and exact mass determination even more difficult and subject to even larger error. This is where this new aspect of the invention may make an even bigger difference by avoiding peak analysis altogether and by taking into consideration other more significant isotopic peaks.

The critical role that comprehensive mass spectral calibration plays in this novel search process will become apparent to one skilled in the art due to its intrinsic capability of making mass spectral peak shapes known, analytically calculatable, or even uniform across a full mass spectral range. It should nonetheless be pointed out that as long as the peak shape function is known, even just in numerical form, this novel searching algorithm can be used through proper replication schemes such as shifting or interpolation. Moreover, if the instrument has been tuned well enough to have its peak shape function resemble a mathematically definable peak shape, this novel searching algorithm can also be used to yield some useful, if not best attainable, results.

Another aspect of this invention is that the fitting residual can be used as a good indicator of whether the mass spectral peak segment contains a single molecule or a linear combination of multiple molecules of very similar masses. FIG. 9A shows a mass spectral isotope profile measured on a higher resolution qTOF instrument after the comprehensive calibration (solid line) and the fitted Reserpine (exact monoisotopic mass 609.2812 Da) theoretical profile (dashed) with residual given in FIG. 9B. FIG. 9C shows the fit with another molecule, alanine 8-mer, with a very similar monoisotopic mass of 609.2972 Da (fitting residual shown in FIG. 9D). When fitting with both reserpine and alanine 8-mer by adding alanine 8-mer into peak component matrix P, the fitting is much improved (FIG. 9E) with the residual much reduced (FIG. 9F). FIG. 10A through FIG. 10F shows the zoomed-in version of FIG. 9A-9F. As a result of WMLR from step 510J in FIG. 5, the regression coefficients represent the relative contribution of each ion into the combined mass spectral profile data, providing quantitative information about the ions involved in addition to qualitative identification information.

The decision to add components into the peak component matrix P is made at step 510L in FIG. 5, typically based on statistical measures from the regression such as fitting residuals relative to known or estimated level of error or noise in data, i.e. above a predetermined level. The step of adding one or more components into the peak component matrix for mixture analysis and identification in a mixture is illustrated as 510M in FIG. 5. When previously added components become statistically insignificant with the addition of other components, a decision can be made to remove one or more components at step 510N based on a similar significance test such, as F-test or t-test, i.e. when below a predetermined level. The step of deleting one or more components from the peak component matrix is illustrated as 510O in FIG. 5. The added or removed components mentioned above may also include baseline component or components or the $1^{st}$ derivative terms mentioned above.

Quantitation of Ions with Interfering Isotopes

In mass spectral experiments involving isotope labeling such as ICAT™ or iTRAQ™ (both marketed by Applied Biosystems, Foster City, Calif.) for quantitation or isotope tracing for metabolism study, there are typically overlapping isotope patterns between the labeled and unlabeled ions or fragments or among the differently labeled or tagged ions or fragments. A good example is the isobaric tags used in iTRAQ™ (WO 20004/070352 A2) where digested peptides from different samples may be labeled with a different reporter tag (with mass of 114.1, 115.1, 116.1, or 117.1), which is attached to a corresponding balance tag of 31, 30, 29, or 28 such that the combined tag has the same nominal mass, allowing for peptides from different samples to be tagged differently with the same added mass. When different samples are mixed, combined, and separated through chromatography prior to mass spectral analysis, the same peptide from different samples would be tagged with tags of the same combined mass, giving the peptide of different tags the same apparent mass in MS analysis where one MS/MS will be performed to break apart the differently tagged peptide ion into a reporter tag, balance tag, the peptide and its fragments during the MS/MS fragmentation. Each reporter tag would now have different mass of 114.1, 115.1, 116.1, or 117.1, the signal intensity of each corresponding to the amount of this peptide in a particular sample before the mixing and combining.

In the 4× multiplexed experiment where four samples are tagged and combined, one expects to observe all four reporters at the 4 masses in MS/MS analysis, the relative intensities of these reporters would indicate the relative amount of the peptide in each of the four samples. Since these tags are only 1 mass unit apart from each other, their isotope patterns would overlap, especially on a lower resolution system such as ABI/Sciex QTRAP.

Another example involves drug metabolism resulting from the dehydrogenation of the parent drug or its fragment where a combined isotope profile from the ion before and after dehydrogenation will be observed. The combined isotope profile is a linear combination of two individual isotope profiles only 2 Da apart from each other with significant overlaps. It is desirable to measure the relative concentration of the dehydrogenated metabolite to that of the parent drug or drug fragment in order to assess the extent of this particular metabolic process.

Figure 11A:
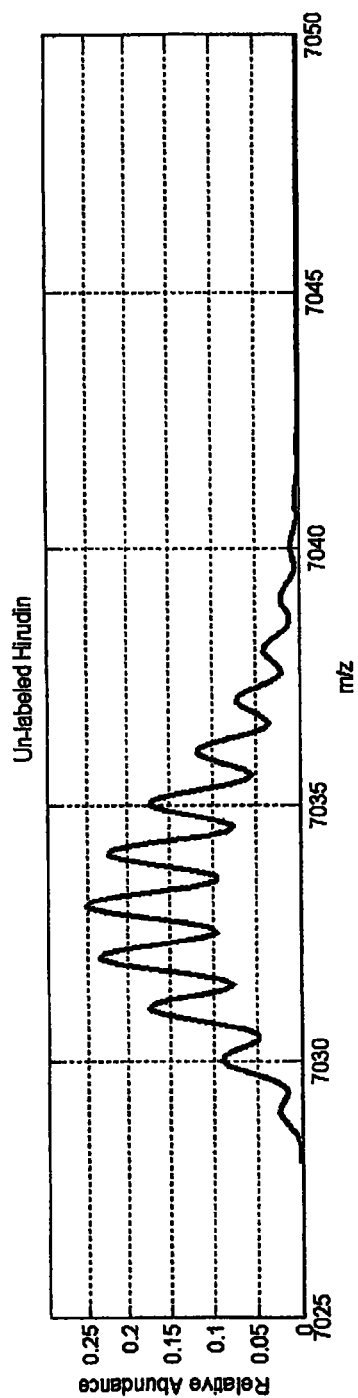
FIG. 11A is the theoretical isotope profile mode data for Hirudin at unit mass resolution.
Figure 11B:
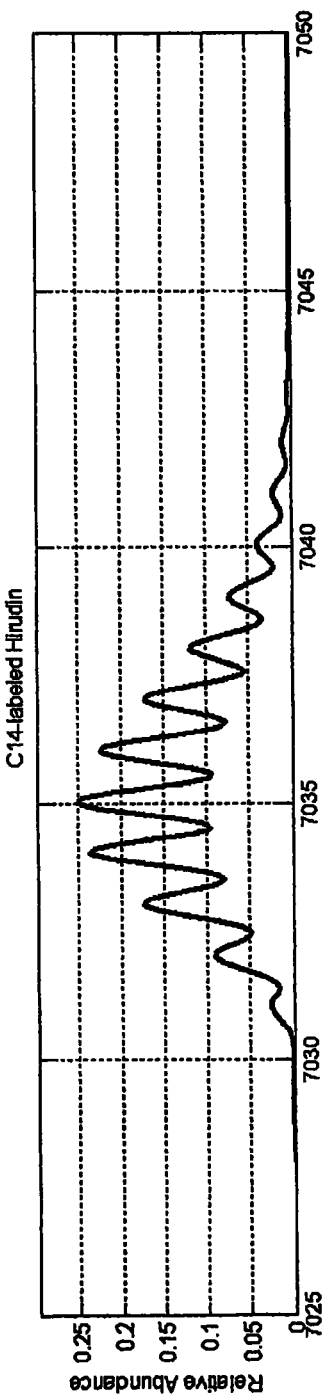
FIG. 11B is the $C^{14}$-labeled version of the data of FIG. 11A.
Figure 11C:
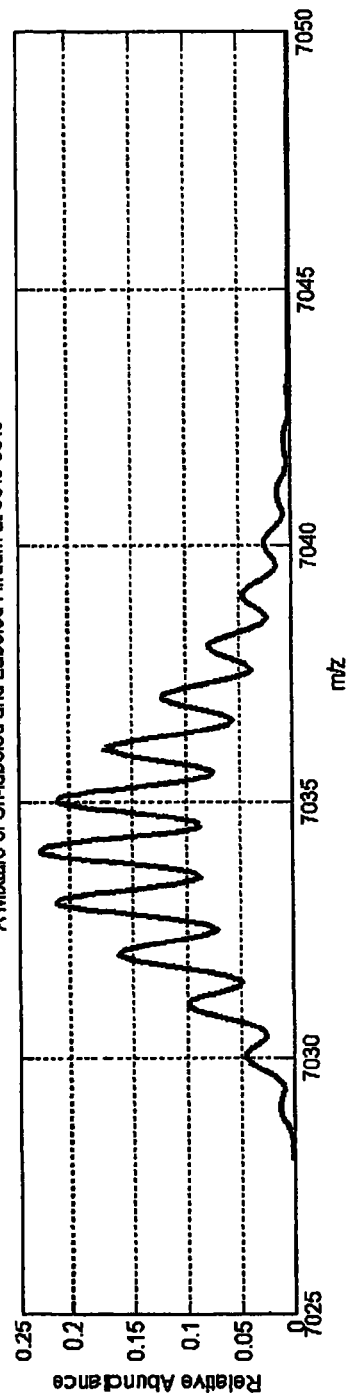
FIG. 11C is the data for a 1:1 mixture of the profiles represented in FIG. 11A and FIG. 11B.

Another example involves mass spectral measurement of a mixture of "cold" and "hot" samples where the "cold" sample refers to an unlabeled sample and "hot" sample refers to a (radio) labeled sample such as $C^{14}$-labeled sample, resulting in an observed mass spectral response composed of two mutually overlapping isotope profiles. FIG. 11A shows the isotope profile from unlabeled Hirudin whereas FIG. 11B shows the isotope profile from a $C^{14}$-labeled Hirudin, all at unit mass resolution. The mass spectral response from the 50%:50% mixture of the unlabeled and labeled Hirudin is shown in FIG. 11C. Due to the high chemical and ionization similarity between the unlabeled and labeled ion, they each serve as a great internal reference to the other when quantitative information is sought after in an analysis. It is therefore highly desirable to quantify the relative concentrations of the unlabeled and labeled ion with overlapping isotope profiles.

In other quantitative mass spectral experiments such as protein or peptide quantification, it is typically required to have a labeled ion far removed from its unlabeled counterpart in terms of m/z so as to minimize the possible cross talk and achieve reliable quantitation. This sometimes requires a complex chemistry process, especially for large molecules where the required separation in m/z is even larger due to the increased peak width of the mass spectrometer and the quickly expanding isotope distribution, as is the case for Hirudin in FIG. 11A-11C.

In this aspect of the invention, a novel and unbiased approach will be taken to quantify each of the ions measured in an overlapping mass spectral range regardless of the m/z separation between or among them, even at unit mass resolution.

Figure 12:
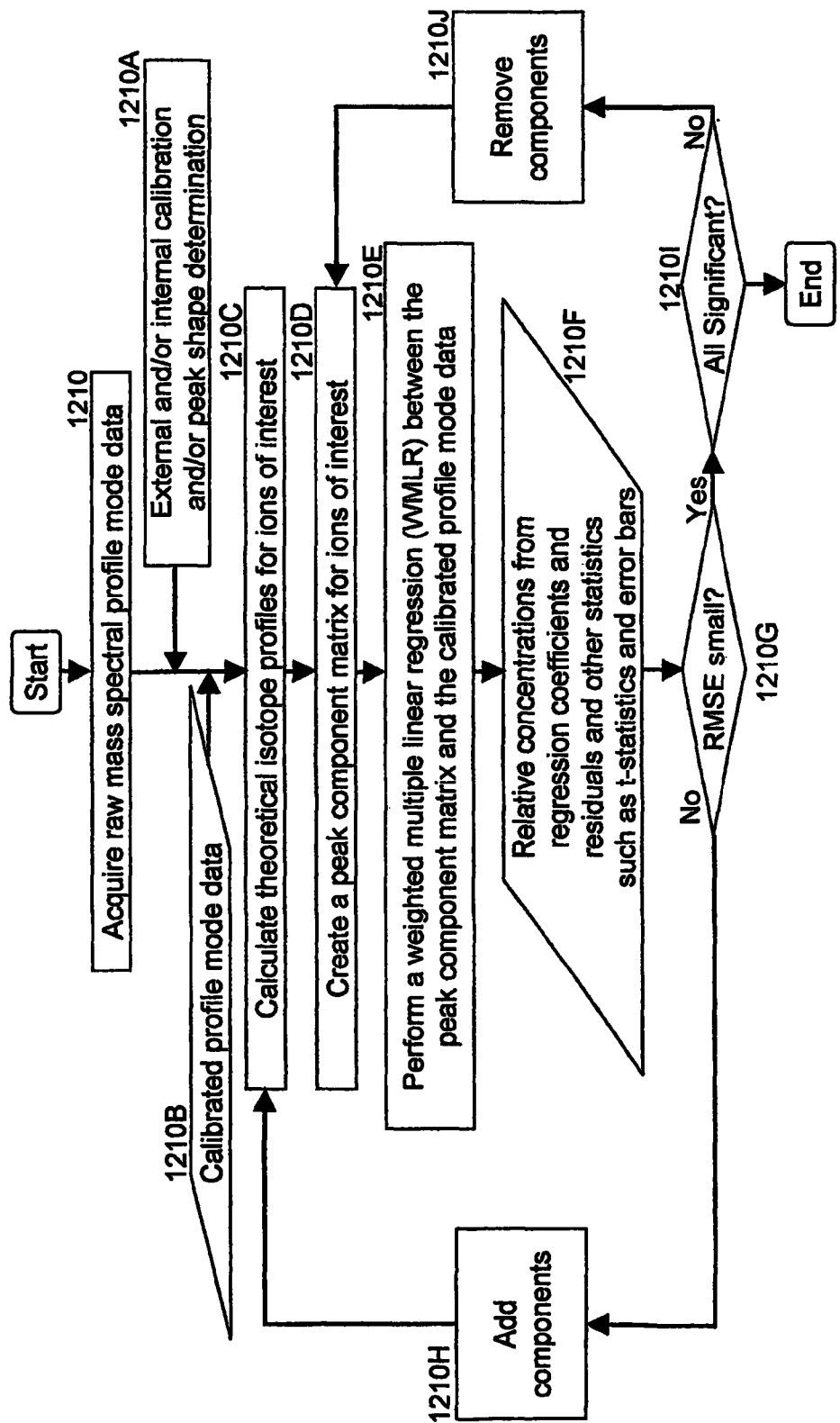
FIG. 12 is a flow chart for the unbiased quantitative analysis process of this invention.

The steps involved are:
1. Acquire raw profile mode data containing all labeled or unlabeled ions and their isotopes in a mass spectral range. This step is illustrated as 1210 in FIG. 12.
2. If applicable, develop an instrument calibration and/or obtain the peak shape functions suitable for the mode of MS operation such as full MS or MS/MS using the comprehensive calibration disclosed in U.S. patent application Ser. No. 10/689,313 filed on 20 Oct. 2003 and PCT/US2004/034618 filed on 20 Oct. 2004 and a United States patent application, filed of even date herewith as U.S. patent application Ser. No. 11/261,440 based on U.S. provisional patent application Ser. No. 60/623,114 filed 28 Oct. 2004. This step is illustrated as 1210A in FIG. 12.
3. If applicable, apply the instrument calibration on the above acquired data to obtain the externally calibrated data and the corresponding weights (pages 29-31 of U.S. patent application Ser. No. 10/689,313 and pages 28-32 in PCT/US2004/034618 filed on 20 Oct. 2004). If necessary, apply internal calibration to the externally calibrated data and obtain the corresponding new weights (pages 29-31 of U.S. patent application Ser. No. 10/689,313 and pages 28-32 in PCT/US2004/034618 filed on 20 Oct. 2004). This step is illustrated as 1210B in FIG. 12.
4. Calculate the theoretical isotope distributions for all ions of interest including native or labeled ions or any known background ions of relevance in this mass range based on their molecular compositions. This step is illustrated as 1210C in FIG. 12.
5. Convolute the theoretical isotope distributions with the target peak shape function specified during instrument calibration or the actual peak shape functions to obtain theoretical isotope profiles for all ions selected. This step is also illustrated as 1210C in FIG. 12.
6. Construct a peak component matrix P (page 32 of U.S. patent application Ser. No. 10/689,313 and page 34 of PCT/US2004/034618 filed on 20 Oct. 2004) to include any linear or nonlinear functions as baseline components and all theoretical isotope profiles calculated above as peak components. This step is illustrated as 1210D in FIG. 12.
7. Perform a Weighted Multiple Linear Regression (WMLR, equation 6 on page 34 of U.S. patent application Ser. No. 10/689,313 and equation 6 on page 35 in PCT/US2004/034618 filed on 20 Oct. 2004) between the calibrated or raw profile mode data and the peak component matrix P. This step is illustrated as 1210E in FIG. 12.
8. Report the regression coefficients as the relative concentrations for each of the components including the baseline and ion components. These relative concentrations are free from each other's interference and thus unbiased due to the WMLR performed. These concentration estimates are also more accurate due to the comprehensive calibration applied and the noise filtering as part of the calibration process when applied. Other well established statistics such as t-values, p-values, F-statistic, correlation coefficients, and residuals can also be reported. This step is illustrated as 1210F in FIG. 12.

When no calibration is available, one may omit steps 2 & 3 and consider a generally accepted peak shape function, either mathematically defined or numerically derived from the measurement of standard ions, as the peak shape function for the convolution operation in step 5. In this case or in the case of external calibration without further internal calibration, there may be significant mass shift between the theoretically calculated isotope profiles (in peak component matrix P) and the actually measured or externally calibrated mass spectral profile data. One may consider adding a first derivative of the measured or externally calibrated mass spectral profile data into the peak component matrix P in step 6 to compensate for this shift without incurring much computational expense.

Sometimes one may have started with too many components including baseline components in the peak component matrix P and find at the end (1210G in FIG. 12) that some of the components may be statistically insignificant (1210I in FIG. 12) and therefore should be removed (1210J in FIG. 12) prior to another round of regression analysis. These insignificant components may include baseline components or $1^{st}$ derivative components mentioned above.

At other times one may find that not enough components have been included due to the large residual (RMSE, 1210G in FIG. 12) and may proceed to add more components (1210H in FIG. 12) for inclusion into the peak component matrix prior to another round of regression analysis.

In both the mass spectral fitting for molecular search and the quantitation of ions with overlapping isotopes, it is conceptually possible to perform a peak analysis involving centroiding prior to the regression step, according to prior art from commercially available systems. As mentioned above, the centroiding process is prone to error due to the deconvolution nature of the operation. In addition, it destroys information from closely located isotopes. Furthermore, it reduces the degrees of freedom for the peak component matrix P and limits the number of ions that can be searched or quantified. For example, on a unit mass resolution system with mass spectral data covering 4 Da mass range of a typical small molecule's isotope profile (such as 401-405 Da mass range for Buspirone in FIG. 6A-6C), typically 4 peaks may be identified as results of peak centroiding, limiting the quantitative or qualitative search power of the centroid data to at most 4 co-existing ions whereas the profile mode quantitation presented above can handle at up to 40 co-existing ions. This profile mode analysis, when performed in the preferred embodiment with the comprehensive mass spectral calibration, can further enhance the analytical capacity from 4 ions to possibly 100-400 co-existing ions in such a narrow mass window due to the high mass accuracy (down to 5-10 mDa mass error) achievable on even unit mass resolution systems.

Although the description above contains many specifics, these should not be construed as limiting the scope of the invention but as merely providing illustrations of some feasible embodiments of this invention.

Thus the scope of the invention should be determined by the appended claims and their legal equivalents, rather than by the examples given. Although the present invention has been described with reference to the embodiments shown in the drawings, it should be understood that the present invention can be embodied in many alternate forms of embodiments. In addition, any suitable size, shape or type of elements or materials could be used. Accordingly, the present invention is intended to embrace all such alternatives, modifications and variances which fall within the scope of the appended claims.

What is claimed is:

1. A method for operating a computer having a computer readable storage medium containing instructions stored therein for causing the computer to analyze data from a mass spectrometer, wherein the instructions cause the computer to perform steps comprising:
    acquiring raw mass spectral data in a profile mode including a plurality of points across a mass spectral peak, from the mass spectrometer, as input to the computer for:
    generating a peak list containing one of peak mass locations and peak mass ranges, said list being representative of candidate ions which may be present;
    calculating a theoretical mass spectral isotope profile for each of the candidate ions;
    forming a peak component matrix for each of the candidate ions identified;
    performing regression analysis involving the peak component matrix for each of the candidate ions and the acquired profile mode data; and
    ranking the candidate ions with a fitting statistic with that ion corresponding to the most significant statistic being the most likely candidate ion present.

2. The method of claim 1, further comprising adding candidate ions into an existing peak component matrix and performing further regression analysis involving an augmented peak component matrix and the acquired profile mode data for mixture analysis, if a fitting residual error is larger than a level of random measurement error.

3. The method of claim 1, further comprising eliminating candidate ions or components and performing further regression analysis involving a reduced peak component matrix and the acquired profile mode data, if a molecule or component does not reduce a fitting residual error beyond a random measurement error.

4. The method of claim 1, further comprising performing a mass spectral calibration using at least one internal calibration standard on the acquired raw mass spectral profile mode data.

5. The method of claim 1, further comprising performing an external calibration on the acquired raw mass spectral profile mode data.

6. The method of claim 5, further comprising applying an internal calibration to said externally calibrated data to obtain externally and internally calibrated data.

7. The method of claim 1, wherein actual peak shape function is transformed to a mathematically definable function prior to said regression analysis.

8. The method of claim 1, wherein the regression analysis is performed with an actual profile data as acquired.

9. The method of claim 1, wherein the regression analysis is performed with an actual profile data as calibrated.

10. The method of claim 1, further comprising:
    applying a total calibration filtering matrix to the raw mass spectral data to correct for mass axis error and to transform mass spectral peak shape function into a target peak shape function; and
    using the target peak shape function to create the theoretical isotope profiles for inclusion in said peak component matrix.

11. The method of claim 10, wherein the total calibration filtering matrix is developed as at least one of an external, instrument, or internal calibration.

12. The method of claim 1, further comprising:
    calculating actual mass spectral peak shape function as part of a calibration process; and
    using the calculated actual mass peak shape function to create the theoretical isotope profile for inclusion in said peak component matrix.

13. The method of claim 1, further comprising:
    approximating actual mass spectral peak shape function as part of an instrument tuning process; and
    using the approximated actual mass peak shape function to create the theoretical isotope profile for inclusion in said peak component matrix.

14. The method of claim 1, wherein candidate ions are selected through search in at least one of a given library, given biotransformation pathways, other reaction pathways, and elemental composition search.

15. The method of claim 1, further comprising adding a first derivative of an acquired or calibrated profile mode data, into the peak component matrix.

16. The method of claim 1, further comprising the exclusion of some sections of the acquired profile mode data for the analysis due to one of poor signal to noise, nonlinearity, and interferences.

17. The method of claim 1, wherein the regressions are performed between an acquired or calibrated profile mode data and each peak component matrix using the inverse of a peak intensity variance as weights.

18. The method of claim 1, wherein calculating the theoretical mass spectral isotope profile for each of the candidate ions identified comprises convoluting the theoretical isotope distribution with one of the target peak shape functions, actual peak shape functions, and approximated peak shape function.

19. The method of claim 1, wherein forming a peak component matrix comprises including any linear or non-linear functions as possible baseline components.

20. The method of claim 1, wherein forming a peak component matrix comprises including theoretical isotope profiles of any already identified ions into said peak component matrix.

21. The method of claim 1, wherein the fitting statistic is calculated as one of t-value, p-value, F-statistic, correlation coefficient, and residuals.

22. A mass spectrometer system, associated with the computer, and operated in accordance with claim 1.

23. The method of claim 1, wherein a different peak component matrix is formed for each of the candidate ions identified.

24. A method for operating a computer having a computer readable storage medium containing instructions stored therein for causing the computer to analyze data from a mass spectrometer, wherein the instructions cause the computer to perform steps comprising:
    acquiring raw profile mode data containing at least one of native and labeled ions with their isotopes in a mass spectral range from the mass spectrometer, as input to the computer for:
    calculating theoretical isotope distributions for all ions of interest including at least one of native and labeled ions based on their molecular compositions;
    convoluting the theoretical isotope distributions with one of calibrated peak shape function, actual peak shape functions, and approximated peak shape functions to obtain theoretical isotope profiles for all ions;
    constructing a peak component matrix of all theoretical isotope profiles calculated as peak components;
    performing a regression analysis involving the acquired profile mode data and the peak component matrix; and
    reporting regression coefficients of the regression analysis as relative concentrations for each of the ions.

25. The method of claim 24, wherein the peak component matrix includes baseline components as linear or nonlinear functions.

26. The method of claim 24, further comprising reporting regression coefficients of the baseline components.

27. The method of claim 24, further comprising reporting statistics of the regression, said statistics including at least one of t-values, p-values, F-statistic, correlation coefficients, and fitting residuals or errors.

28. The method of claim 24, further comprising:
    adding theoretical isotope profiles of candidate ions or other components; and
    performing further regression analysis involving the acquired profile mode data and the augmented peak component matrix, if the fitting residual or error is significantly larger than a predetermined amount.

29. The method of claim 24, further comprising eliminating candidate ions or components and performing further regression analysis involving the acquired raw profile mode data and the reduced peak component matrix, if a molecule or component is deemed to be statistically insignificant.

30. The method of claim 24, further comprising performing a calibration using at least one internal calibration standard to transform the acquired raw profile mode data prior to regression analysis.

31. The method of claim 24, further comprising applying at least one of internal and external calibration to at least one of acquired raw and calibrated profile mode data to obtain at least one of externally and internally calibrated data and thereby transform the acquired raw profile mode data prior to regression analysis.

32. The method of claim 24, wherein actual peak shape function is transformed to a mathematically definable target peak shape function through at least one of external and internal calibration.

33. The method of claim 24, wherein the regression analysis is performed with an actual profile mode data as acquired.

34. The method of claim 24, wherein the regression analysis is performed with an actual profile mode data as calibrated.

35. The method of claim 24, further comprising:
    applying a total calibration filtering matrix to the raw mass spectral data to correct for mass axis error and to transform mass spectral peak shape function into a target peak shape function; and
    using the target peak shape function to create the theoretical isotope profiles for inclusion in a peak component matrix.

36. The method of claim 35, wherein the total calibration filtering matrix is developed as at least one of an external, instrument, and internal calibration.

37. The method of claim 24, further comprising:
    calculating actual mass spectral peak shape function as part of a calibration process; and
    using the calculated actual mass peak shape function to create the theoretical isotope profile for inclusion in a peak component matrix.

38. The method of claim 24, further comprising:
    approximating actual mass spectral peak shape function as part of an instrument tuning process; and
    using the approximated actual mass peak shape function to create the theoretical isotope profile for inclusion in a peak component matrix.

39. The method of claim 24, further comprising adding a first derivative of the acquired raw profile mode data or calibrated profile mode data, into the peak component matrix.

40. The method of claim 24, wherein the regression analysis is performed between the profile mode data and peak component matrix using the inverse of profile mode intensity variance as weights.

41. The method of claim 24, wherein calculating the theoretical mass spectral isotope distribution for each of the ions to be included comprises convoluting the theoretical isotope distribution with one of target peak shape functions, actual peak shape functions, and approximated peak shape functions.

42. The method of claim 24, wherein forming a peak component matrix comprises including the theoretical isotope profiles of any already identified background ions into said peak component matrix.

43. The method of claim 24, wherein the ions with their isotopes are overlapped with each other in a mass spectral range.

44. The method of claim 24, further comprising performing a peak analysis or centroiding step on both the acquired or calibrated profile mode data and theoretical isotope profiles prior to forming the peak component matrix and regression analysis.

45. A mass spectrometer system, associated with the computer, and operated in accordance with claim 24.

46. A non-transitory computer readable storage medium containing computer instructions stored therein for causing a computer to perform steps comprising:

acquiring, from a mass spectrometer, raw mass spectral data in a profile mode including a plurality of points across a mass spectral peak, as input to the computer;

generating a peak list containing one of peak mass locations and peak mass ranges, said list being representative of candidate ions which may be present;

calculating a theoretical mass spectral isotope profile for each of the candidate ions;

forming a peak component matrix for each of the candidate ions identified;

performing regression analysis involving the peak component matrix for each of the candidate ions and the acquired profile mode data; and ranking the candidate ions with a fitting statistic with that ion corresponding to the most significant statistic being the most likely candidate ion present.

47. The non-transitory computer readable storage medium of claim 46, further comprising computer instructions stored therein for causing the computer to perform the further step comprising: forming a different peak component matrix for each of the candidate ions identified.

48. A non-transitory computer readable storage medium containing computer instructions stored therein for causing the computer to perform steps comprising:

acquiring, from a mass spectrometer, raw profile mode data containing at least one of native and labeled ions with their isotopes in a mass spectral range, as input to the computer;

calculating theoretical isotope distributions for all ions of interest including at least one of native and labeled ions based on their molecular compositions;

convoluting the theoretical isotope distributions with one of calibrated peak shape function, actual peak shape functions, and approximated peak shape functions to obtain theoretical isotope profiles for all ions;

constructing a peak component matrix of all theoretical isotope profiles calculated as peak components;

performing a regression analysis involving the acquired profile mode data and the peak component matrix; and reporting regression coefficients of the regression analysis as relative concentrations for each of the ions.

* * * * *